United States Patent [19]
Alexander

[11] Patent Number: 5,257,419
[45] Date of Patent: Nov. 2, 1993

[54] ABDOMINAL SUPPORT BELT

[75] Inventor: William K. Alexander, Knoxville, Tenn.

[73] Assignee: American Powersports Products, Inc., Knoxville, Tenn.

[21] Appl. No.: 883,264

[22] Filed: May 14, 1992

[51] Int. Cl.$^5$ .............................................. A61F 6/02
[52] U.S. Cl. ............................................ 2/44; 2/338; 450/155; 602/19
[58] Field of Search ...................... 2/2, 16, 44, 46, 92, 2/102, 311, 312, 338; 450/155; 602/19; 128/100.1, 101.1, 121.1, 96.1

[56] References Cited

U.S. PATENT DOCUMENTS

| | | | |
|---|---|---|---|
| 763,683 | 6/1904 | Magoris | 450/155 X |
| 1,604,076 | 10/1926 | Risselt | 450/155 X |
| 2,360,032 | 10/1944 | Amyot | 450/109 |
| 3,013,919 | 12/1961 | Bialy | 2/338 |
| 3,194,242 | 7/1965 | Marchisella | 450/109 |
| 3,441,027 | 4/1969 | Lehman | 128/578 |
| 3,544,408 | 12/1970 | Loew | 2/338 |
| 3,548,817 | 12/1970 | Mittasch | 602/19 X |
| 3,570,480 | 3/1971 | Stubbs | 602/19 |
| 3,812,862 | 5/1974 | Bernstein | 128/578 |
| 3,920,008 | 11/1975 | Lehman | 128/578 |
| 4,099,524 | 7/1978 | Cueman et al. | 602/19 |
| 4,273,130 | 6/1981 | Simpson | 128/327 |
| 4,390,014 | 6/1983 | Forman | 128/78 |
| 4,509,214 | 4/1985 | Shea | 2/322 |
| 4,555,811 | 12/1985 | Shimalla | 2/51 |
| 4,703,750 | 11/1987 | Sebastian et al. | 2/338 X |
| 4,836,194 | 6/1989 | Sebastian et al. | 128/78 |
| 5,005,216 | 4/1991 | Blackburn et al. | 2/79 |
| 5,040,524 | 8/1991 | Votel et al. | 2/310 X |
| 5,070,866 | 12/1991 | Alexander et al. | 128/78 |
| 5,081,748 | 1/1992 | Eberle | 24/442 |
| 5,111,806 | 5/1992 | Travis | 602/19 |
| 5,122,111 | 6/1992 | Sebastian et al. | 128/112.1 |
| 5,148,549 | 9/1992 | Sydor | 2/48 X |

Primary Examiner—Clifford D. Crowder
Assistant Examiner—Jeanette E. Chapman
Attorney, Agent, or Firm—Luedeka, Hodges, Neely & Graham

[57] ABSTRACT

An abdominal support belt of the type which includes an elongated flat waist band adapted to encircle the waist of a user and one or more supplemental elastic (resilient) strap or straps having unattached ends adapted to be grasped and drawn toward the anterior midline of the user's abdomen and releasible secured to the waist band when the belt is secured about the waist of the user for enhancing the support provided by the belt, and including one or more devices for limiting the extent of return of the strap or straps when the unattached end thereof is released from the waist band and the strap or straps is permitted to return toward its relaxed state. The belt further includes improved wear resistance and shape retention properties, particularly associated with the opposite ends of the waist band.

11 Claims, 7 Drawing Sheets

ABDOMINAL SUPPORT BELT

FIELD OF THE INVENTION

The present invention relates to abdominal support belts generally. More specifically, the present invention relates to an abdominal support belt of the type which includes an elongated flat waist band and one or more supplemental elastic tensioning straps which overlie the waist band. When the straps are stretched to the desired tension, the ends of the straps are releasible secured to the waist band to enhance the support provided by the belt.

BACKGROUND OF THE INVENTION

Participation in various activities, such as lifting, often places a considerable strain on the lower back. Efforts to alleviate such back strain problems have been directed to abdominal support belts which are placed about the waist of the participants prior to engaging in an activity that possibly will introduce strains to the back.

It is generally accepted that the wearing of a properly designed abdominal support belt can significantly reduce the risk of back injury, especially in combination with the practice of good body mechanics, generally accepted lifting techniques and sound physical conditioning. Properly designed belts are those belts which are fitted to the individual user in a manner which permits the selection by the user of the degree of support required for the task at hand.

One type of abdominal support belt provides a waist band having overlapping ends which are detachably connectable, such as by mated hook and loop fabric, and a tensioning strap in the form of an elastic band that overlies the waist band having opposite ends which are detachably connectable, such as by mated hook and loop fabric, to the waist band. In a preferred embodiment, the tensioning strap is anchored intermediate its opposite ends to the waist band at locations such that the anchor overlies the spinal column of the wearer. Prior to activity, the waist band is positioned around the waist of the user and the ends of the waist band are connected in an overlapping relationship to secure the belt about the waist of the user. The tensioning strap is then stretched a desired amount by pulling each end of the tensioning strap toward the anterior midline of the user's abdomen. The ends of the tensioning strap are then connected to the waist band to secure the tensioning strap in its tensioned state which corresponds to the degree of support required for the task at hand. Such belts, however, have several disadvantages. For example, the ends of the waist band experience noticeable wear after relatively few uses. Particularly, the ends of the waist band exhibit a worn or weathered appearance and often curl inwardly. Another disadvantage of such belts is that the ends of the tensioning strap are inconveniently located and are hard to reach for the user when putting on the belt. In addition the ends of the tensioning band recoil strongly when released and often strike the user. This recoil can also cause the hook material on the end of the tensioning strap to contact the waist band and cause additional wear, particularly along the side edges of the waist band with resultant premature deterioration of the waist band.

Accordingly, there is a need in the art for an improved support belt which permits the selection by the user of the degree of support desired, and which offers improved ease of use and durability.

SUMMARY OF THE INVENTION

It is an object of the present invention to provide an improved support belt wherein the degree of support desired can be selectively controlled by the user.

It is another object of the present invention to provide an improved support belt having one or more supplemental elastic straps which may be used to provide enhanced support.

It is a further object of the present invention to provide a support belt having supplemental elastic straps for releasably securing to the belt to provide enhanced support and having devices for limiting the extent of return of the elastic straps when they are released.

Generally described, the present invention provides an improved abdominal support belt of the type that includes an elongated substantially flat waist band having opposite ends and being adapted to encircle the waist of a user and be releasably secured thereabout with one of the flat surfaces of the waist band adjacent the user's waist and the other and opposite flat surface thereof facing outwardly of the user's waist. The waist band receives thereon one or more elastic tensioning straps which are anchored generally centrally of the length dimension of the waist band and at a location generally overlying the spinal column of the user when the belt is in place about the waist of the user. Each of the one or more elastic straps has a unattached end extending from the central anchor location toward the anterior of the user's waist and terminates short of the vertical midline of the anterior wall of the user's abdomen, and means for releasably securing the unattached ends of the tensioning strap or straps to the waist band so that when the tensioning strap or straps are stretched and the opposite ends thereof are secured to the waist band near the anterior midline of the abdomen of the user, there is enhanced support provided to the abdomen and/or back of the user. In one embodiment restraints are associated with the waist band for limiting the extent of return of the stretched tensioning strap or straps in a direction toward the user's spinal column when the unattached ends of the strap or straps are released from their stretched state.

In accordance with one aspect of the present invention, the restraints associated with the waist band are in the form of a loop secured to the waist band. The tensioning strap is threaded through the loop and can slide relative to the fixed loop. In a further aspect of the invention, the position of the loop on the waist band is selected so as to prevent full return of the tensioning strap to a relaxed state when the strap is threaded through the loop. In this embodiment, the unattached end of the tensioning strap is provided with means suitable to preclude the unattached end of the belt from passing through the loops upon release of the strap end from its point of securement to the waist band near the abdominal midline and attempted return of the loose strap toward its relaxed state. In one embodiment this means on the unattached end of the strap may be a semi-rigid piece of vinyl which is secured to the end of the strap as by stitching and which is wrapped around the strap end to thereby provide protection against wear on the strap end, as well as to provide a type of handle which may be readily grasped by the wearer for use in pulling on the strap and to stretch the tensioning strap toward the abdominal midline where the end is releasably secured to the waist band. Unexpectedly, the present inventor discovered that when the location of the loop on the waist band was selected such that full relaxation of the strap does not occur prior to the handle contacting the loop upon attempted relaxation of the strap, the tension forces in the strap, in combination with the inability of the handle to pass through the loop, causes the handle to project outwardly from the waist band and in a most convenient position for grasping by the user where the strap is to again be pulled toward its tensioned supporting state. Accordingly, the length of a relaxed strap is chosen so that the loop may be provided approximately halfway between the spinal column and the anterior midline of the wearer where the belt is applied. This arrangement is repeated from each unattached end of the tensioning strap or straps.

Another embodiment of the invention includes resilient, bendable stays located in the end sections to inhibit curling of the ends. In still another embodiment, portions of the end sections are provided by an expanded cast polyvinyl chloride/polyester material. The polyvinyl chloride/polyester material has sufficient body to maintain the generally planar flat geometry of the end section yet is pliable so as to allow the end sections to conform to the waist of the user.

Other and further objects, features and advantages of the present invention will become obvious upon an understanding of the illustrative embodiment about to be described or will be indicated in the appended claims and various advantages not referred to herein will occur to one skilled in the art upon employment of the invention in practice.

DETAILED DESCRIPTION OF A PREFERRED EMBODIMENT

Figure 1:
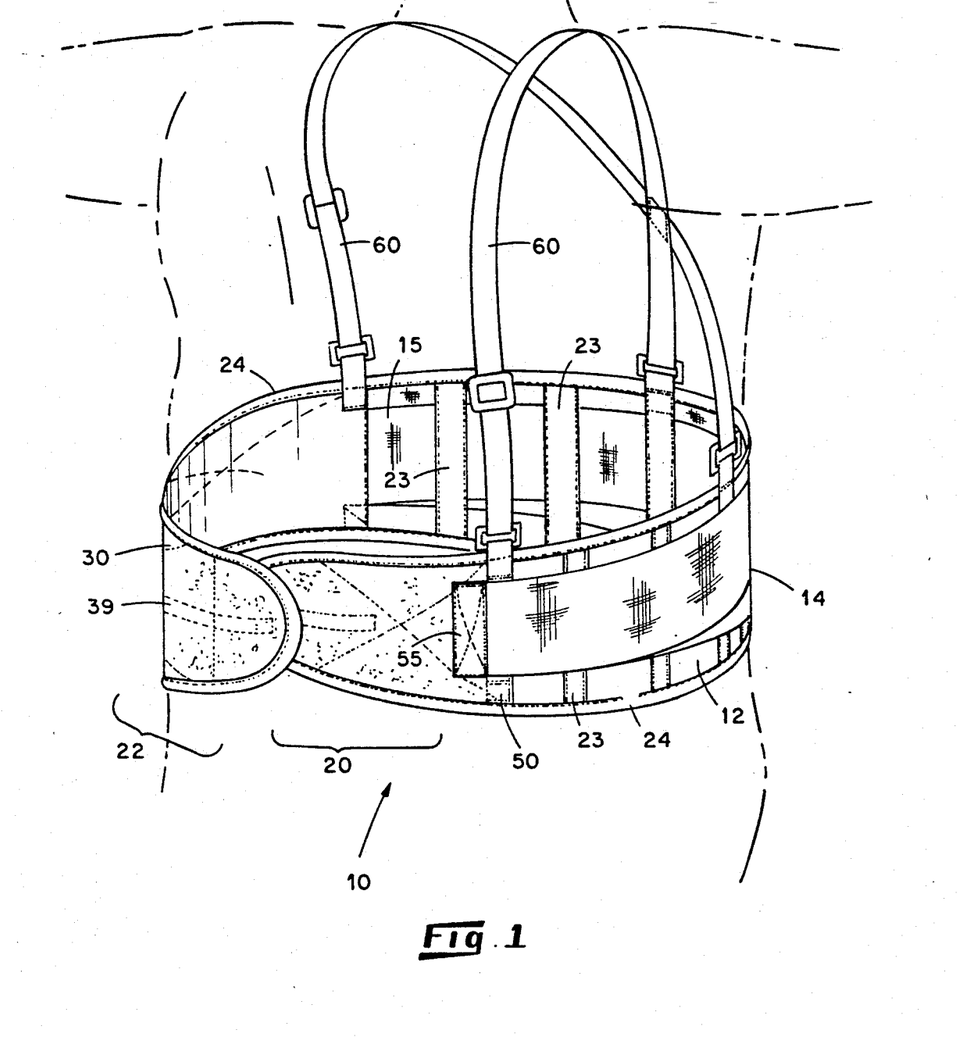
FIG. 1 is a perspective view of an abdominal support belt embodying various of the features of the present invention.
Figure 2:
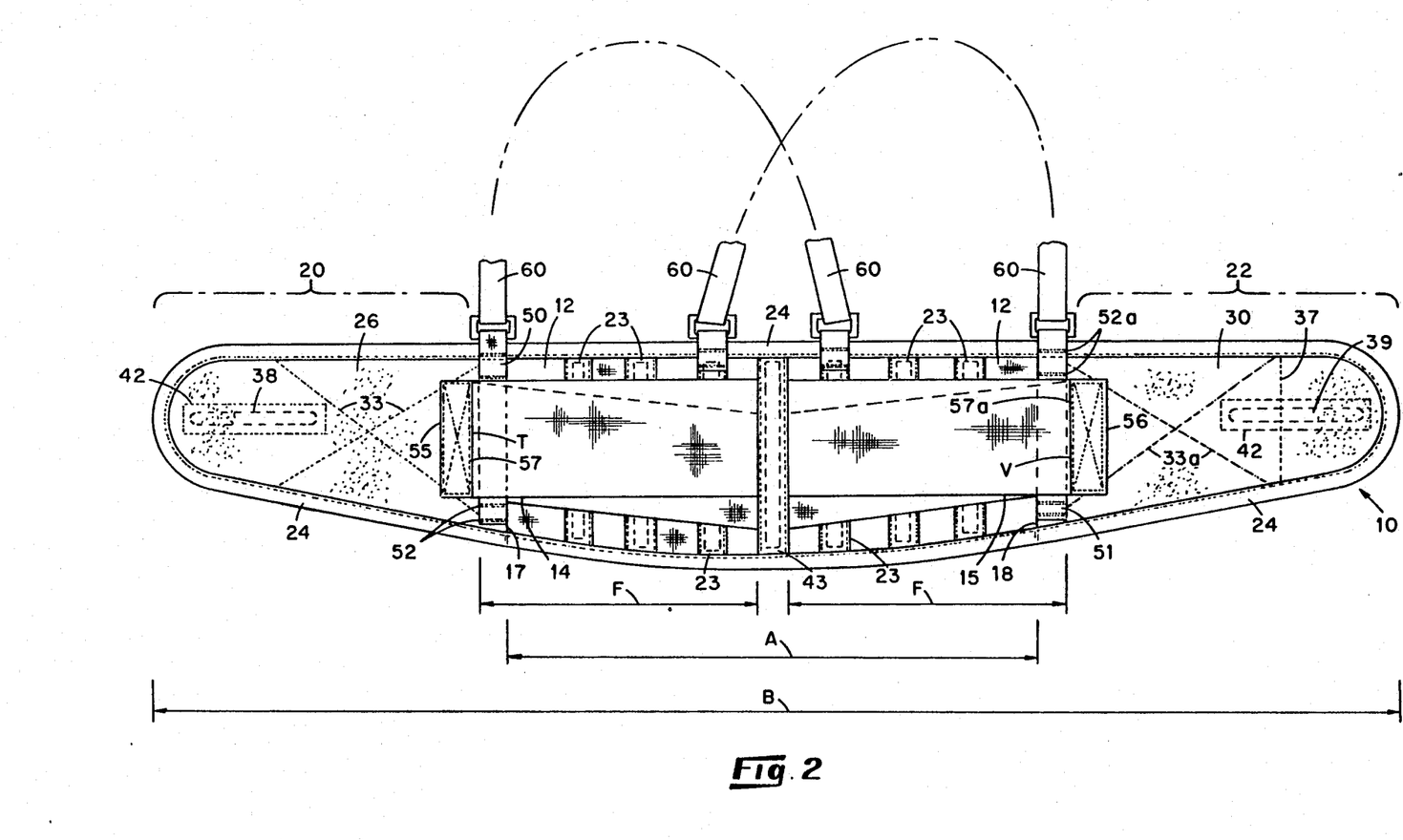
FIG. 2 is a front view of the belt of FIG. 1.
Figure 3:
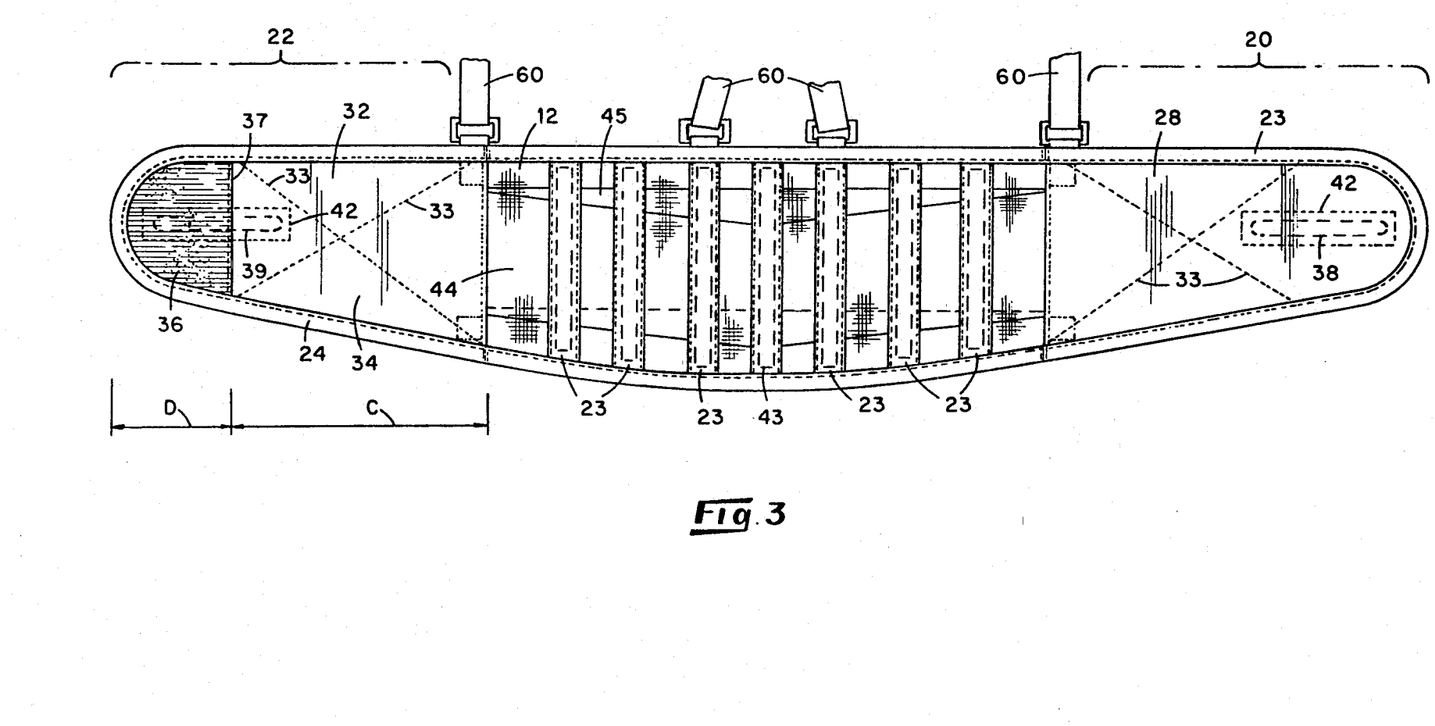
FIG. 3 is a back view of the belt of FIG. 1.

With reference to the accompanying drawings where like features are identified by like reference characters, FIGS. 2 and 3 illustrate front and back views, respectively, of an abdominal support belt 10 constructed in accordance with the present invention and shown in perspective view in FIG. 1. The belt 10 includes an elongated, substantially flat waist band 12 having a length A and a pair tensioning straps 14 and 15 formed of an elastic (i.e. resilient) material and positioned to overlie the waist band 12. To use the belt, the user encircles the waist band 12 about the abdomen and grasps handles 55 and 56 provided at the unattached opposite ends of the tensioning straps 14 and 15 to stretch or tension the tensioning straps. The ends of the tensioning straps are then secured to the waist band 12 while the straps are in the tensioned state to provide the desired degree of support. The present invention includes one or more recoil restraints e.g. loops 50 and 51 for limiting the extent of return of the stretched tensioning straps upon release of their ends.

The waist band 12 includes opposed ends 17 and 18, to which end sections 20 and 22, respectively, are attached, such as by stitches. A plurality of uniformly spaced apart cross members 23 are provided along the length of the band 12 and span the width of the band 12. The cross members 23 are preferably provided by blunt end corset stays covered with a polypropylene web. Suitable corset stays are those available under Product No. 5"×⅜" spiral wire stay from Henry Stuart Co. of Milford, Conn. Optionally, a skid resistant strip may be provided on the inner surface of each cross member 23 to provide a frictional surface between the waist of the user and the cross members to reduce slippage of the waist band 12 with respect to the wearer's waist. Each skid resistant strip is preferably provided by a 15/16 inch wide strip of a polyester material known as GRIP-TEX, available from Medical Textiles of So. Boston, Pa. The mid portion of the waist band 12 is preferably formed of a woven nylon material known as POWERKNIT available from Darlington Fabric Corp. of Atlanta, Ga. and is readily provided in any longitudinal length which, in combination with the waist band end sections 20 and 22, will generally correspond to the girth of the belt user. The waist band 12 is preferably tapered such that its width is about 6 inches in the center of the waist band and about 4 inches at the ends of the waist band. Alternatively, a flat elastic band having a width of between about 3 and 6 inches may be used. The total length B of the belt 10 (i.e., the combined length of the waist band 12 and of the end sections 20 and 22) is preferably slightly greater than that of the waist of the user so that the end sections 20 and 22 may be overlapped to encircle the waist, as shown in FIG. 1. For example, for a waist size of about 36 inches, the length A of the mid portion of the waist band 12 is preferably about 24 inches and each of the end sections 20 and 22 is about 11 inches such that the total length B of the belt is about 35 inches.

The peripheral edges of the belt 10 are preferably covered with a suitable binding 24 stitched onto the edges of the mid portion and the end sections 20 and 22 of the waist band with any suitable thread such as nylon. A preferred binding is a one inch non-stretchable woven nylon binding available from John Solomon Corp. of Sommerville, Md. While this particular binding is preferred, it will be clear that the binding 24 may be made of any suitable material. The binding 24 is normally of a width of about one inch so that it can overlap the front or face and the back of the band 12 and the end sections 20 and 22 and is of sufficient length so as to extend around the peripheral edges of the band 12 and the end sections 20 and 22. This binding serves to provide a smooth, non-irritating edge for the waist band and to protect the peripheral edge of the waist band from normal wear and tear during use of the belt. In particular the binding reduces the likelihood of breakage, such as through wear or by snagging, of one or more of the strands or yarns of the waist band, and subsequent destructive unraveling of the waist band.

Figure 4:
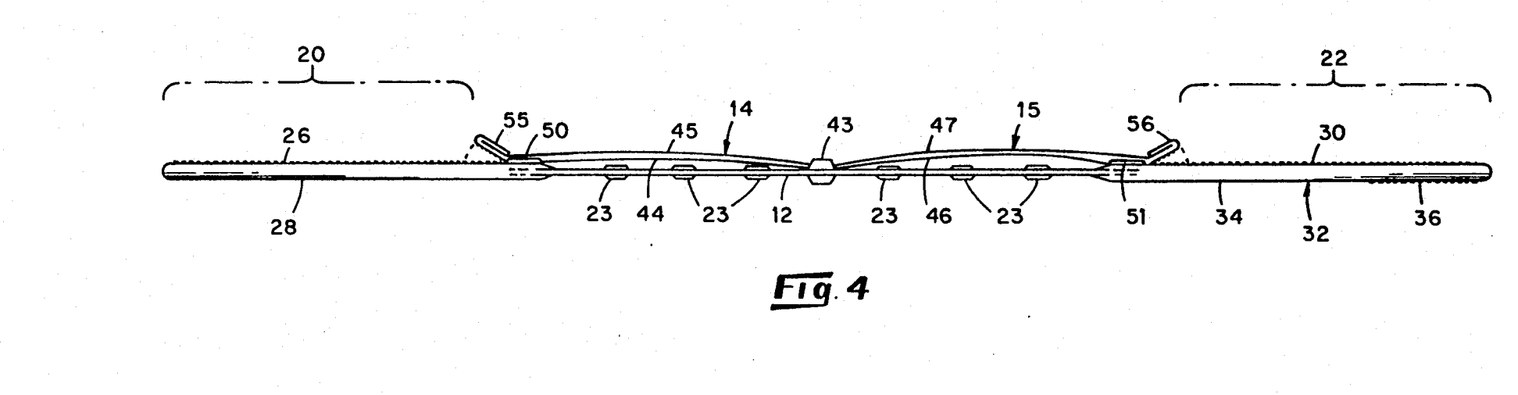
FIG. 4 is a side view of the belt of FIG. 1.

With continued reference to FIGS. 2 and 3, and with reference to FIG. 4, the end section 20 of the waist band 12 has a front surface 26 and a back surface 28, and the end section 22 has a front surface 30 and a back surface 32. An X-shaped line of stitches 33 is preferably provided on each end section to secure the front surface of each end section to its corresponding back surface. As will be explained more fully below, the waist band 12 is encircled about the waist of the user and the end sections 20 and 22 are overlapped and releasible secured to one another to secure the waist band around the waist. To this end, the front surface 26 of the end section 20 and the front surface 30 of the end section 22 are each formed of a loop material, with a preferred loop material being APLIX, available from Aplix of Charlotte, North Carolina. The back surface 28 of the end section 20 is provided by a laminar substrate formed of an expanded cast polyvinyl chloride (PVC) material stitch bonded to a polyester nonwoven substrate. A preferred PVC/polyester laminate material is that known as 2207-68, having a thickness of about $\frac{1}{8}$ inch, available from Ouimet Corporation of Nashville, Tennessee. The back surface 32 of the end section 22 provides an intermediate section 34 located adjacent to the band 12 having a length C, and a tip section 36 adjacent the inner section 34 opposite the band 12 having a length D. As mentioned earlier, for a waist size of about 36 inches, the length A of the mid portion of the waist band 12 is preferably about 24 inches and each of the end sections 20 and 22 is about 11 inches such that the total length B of the belt is about 35 inches. For this belt size, the length C is preferably about $7\frac{1}{2}$ inches and the length D is preferably about $3\frac{1}{2}$ inches. The intermediate section 34 of the end section 22 is also preferably formed of a PVC/polyester material, such as 2207-68. The tip section 36 of the end section 22 is formed of a hook material known in the art as VELCRO and available from Velcro USA of Manchester, New Hampshire.

In a preferred embodiment, the PVC/polyester material of the intermediate section 34 of the end section 22 extends underneath the hook material of the tip section 36 and the tip section 36 is secured over the PVC/polyester material by stitches 37. This design of the end section 22 of the waist band provides for sufficient flexing of the end section as permits conformance of the waist band to the wearer's anatomy while also imparting sufficient rigidity to the end section 22 as causes the end section to retain its generally planar flat geometry. This latter condition aids in prolonging the useful life of the belt.

Figure 8A:
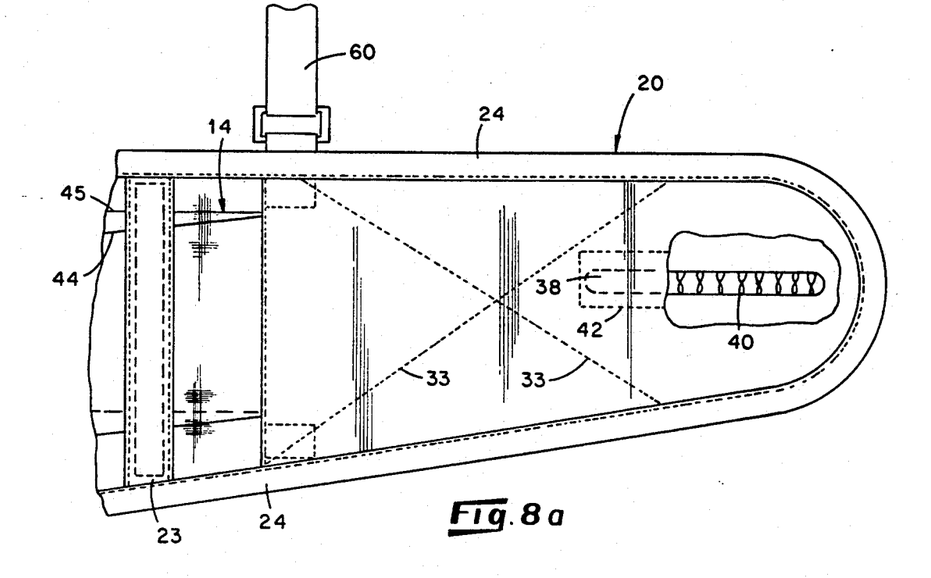
FIGS. 8(a) and 8(b) are cut away views of the front and back, respectively, of an end section of the belt showing the positioning of a stay.
Figure 8B:
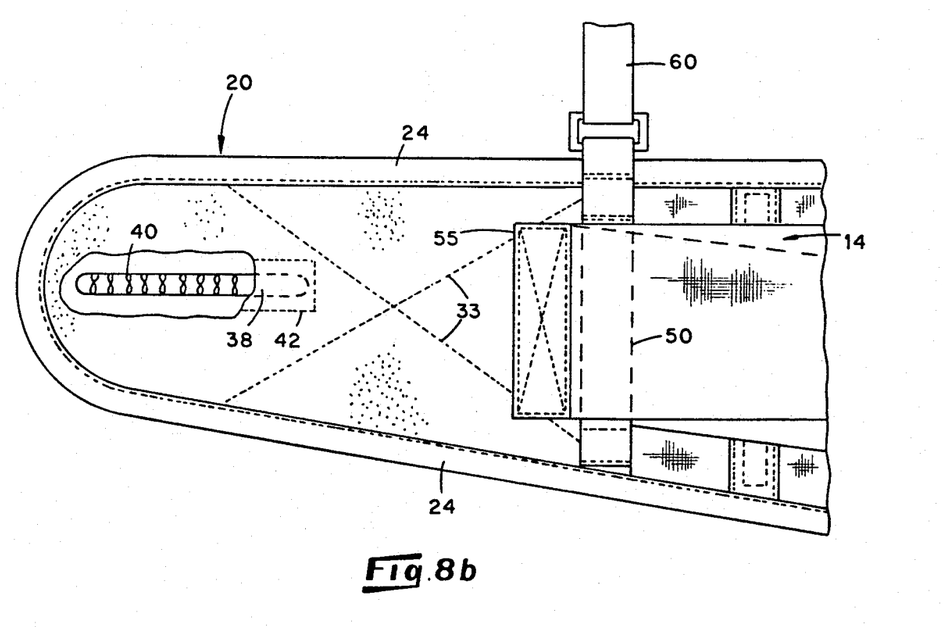

With further reference to FIGS. 2 and 3 and with reference to FIGS. 8(a) and 8(b), a resilient bendable stay 38 is provided in the end section 20 between the front surface 26 and the back surface 28, and a like stay 39 is provided in the end section 22 between the front surface 30 and the back surface 32. These stays 38 and 39 provided in the end sections 20 and 22 of the waist band maintain the end sections in a planar or flat orientation during application of the belt about the waist and inhibit deleterious curling of the end sections which typically occurs in abdominal support belts after extended use. A preferred stay is a spring loaded, rounded end corset stay, $4\frac{1}{4}" \times \frac{3}{8}"$ spiral wire stay, available from Henry Stuart, Inc. of Milford, Connecticut. As shown in FIGS. 8a and 8b, the preferred stay includes linked coils 40 which cooperate to enable the stay to reflex in one direction and bend in the other. Each stay 38 and 39 is preferably secured by stitches 42 within the end sections 20 and 22 and is oriented such that the coils 40 inhibit the end sections from curling, especially inwardly, i.e. in the direction of the back surfaces 28 and 32.

Figure 5:
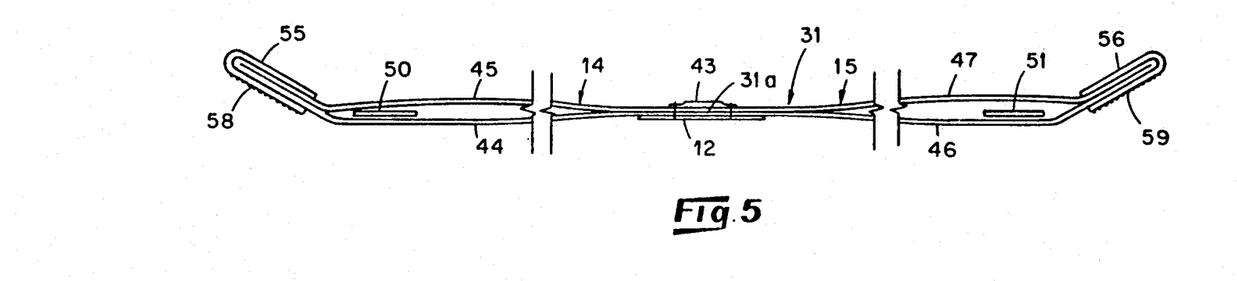
FIG. 5 is a cross-sectional view of one embodiment of a tensioning strap utilized in the belt of the present invention.

With reference now to FIGS. 2, 4, 5, 6, and 7, the tensioning straps 14 and 15 are preferably provided by a single length of elastic material formed into a continuous loop 31 by securing the length to itself along a seam 31a. The loop 31 is centrally anchored to the waist band 12 by an anchoring member 43 which bisects the loop to define the pair of tensioning straps 14 and 15. The anchoring member 43 is located generally centrally of the length dimension of the waist band 12 and at a location generally overlying the spinal column of the user of the belt when the belt is placed about the waist of the user. The anchoring member 43 may be provided by a rounded end corset stay like stay which defines cross member 23. A skid resistant strip, such as GRIPTEX, may optionally be provided on that surface of the member 43 which is positioned adjacent the waist. The loop 31 which provides the tensioning straps 14 and 15 is preferably of an elastic material/polyester available from Medical Textiles, Inc. of South Boston, Virginia under Product No. 102. As best shown in FIGS. 4 and 5, the strap 14 is loop-shaped and has an inner section 44 which is positioned adjacent the waist band 12 and an outer section 45 overlying the inner section 44. The strap 15 is likewise loop-shaped and has an inner section 46 which is positioned adjacent the waist band and an outer section 47 overlying the inner section 46. The strap 14 is positioned to be generally extendable from its anchored location overlying the spinal column in the direction of the end section 20 and the strap 15 is positioned to be generally extendable from the anchor location in the direction of the end section 22.

Figure 9:
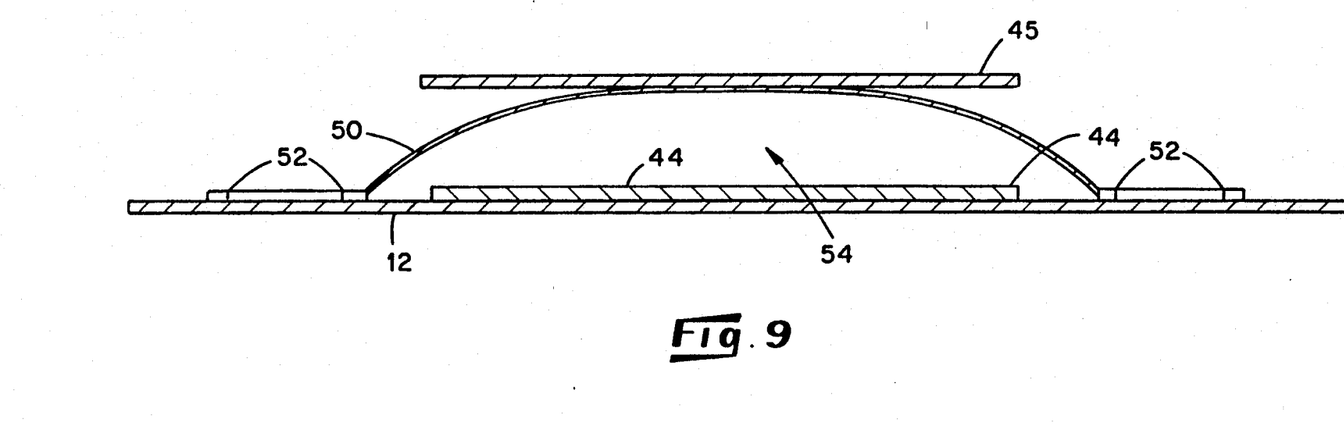
FIG. 9 is a cross-sectional view of a recoil restraint utilized in accordance with the present invention.

With reference to FIGS. 2 and 4, in one embodiment, a pair of recoil restraints 50 and 51 in the form of loops are provided on the waist band 12 for receiving therethrough the inner sections 44 and 46 of the tensioning straps 14 and 15, respectively, in the area between the inner section and outer section of each of the straps 14 and 15. By this means, the extent of return or recoil of the tensioning straps when they are detensioned is limited by engagement of the handles 55 and 56 with the restraints 50 and 51. The depicted recoil restraints 50 and 51 are provided by a strip of a semi-rigid material, such as polyester, positioned across the width of the waist band preferably in the nature of a "belt loop". The recoil restraints are each preferably positioned a distance F from the anchoring member 43 at opposite ends of the waist band adjacent to the end sections 20 and 22. The distance F is chosen to accommodate the length of the straps 14 and 15 so that the straps 14 and 15 remain slightly tensioned when they are "relaxed" and arrested by the restraints 50 and 51, as will be explained more fully below. For example, for a belt sized to fit a 36 inch waist, the straps 14 and 15 are each preferably about 11 inches in length in the slack or completely relaxed state and the distance F is chosen to be about 13 inches. The depicted recoil restraints 50 and 51 each have a width of about 1 inch and a length which is preferably less than the width of the waist band 12 and slightly greater than the width of the straps 14 and 15 so that the straps 14 and 15 may freely move within the recoil restraints 14 and 15 during extension and retraction (to the permitted extent) of the straps. As shown in FIG. 9, the opposite ends of the recoil restraint 50 are secured to the waist band by stitches 52, as in the same manner that belt loops are attached to an article of clothing, such that a channel 54 is defined between the waist band 12 and the recoil restraint 50. The restraint 51 is likewise secured to the waist band by stitches 52a to provide a channel (not shown). Thus it will be appreciated that each tensioning strap may move freely and independently within the channel 54 of its respective recoil restraint as it is being stretched in a direction generally away from the anchoring member 43 or as it retracts toward its relaxed state.

Figure 6:
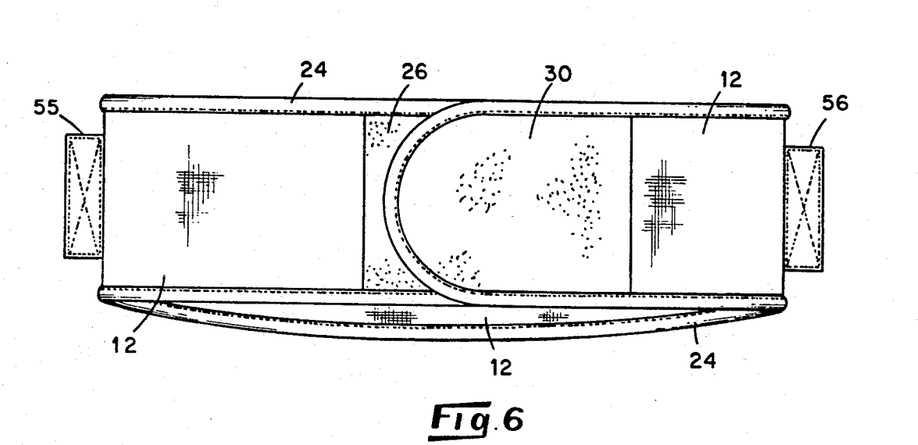
FIG. 6 is a front elevational view of the belt of FIG. 1 showing the tensioning strap in an relaxed state, with the handles extending outwardly from the waist band and easily accessible for grasping to tension the strap.

With further reference to FIG. 9, the inner section 44 of the tensioning strap 14 extends between the restraint 50 and the waist band 12 through the channel 54 defined between the recoil restraint 50 and the waist band 12, and the outer section 45 of the tensioning strap 14 passes above the restraint 50. The inner section 46 and the outer section 47 of the tensioning strap 15 are arranged relative to the restraint 51 in the same manner as the strap 14 above. As best shown in FIGS. 4 and 5, a handle 55 is attached, such as by stitches 57, to the unattached end of the tensioning strap 14 along an attachment path T located outwardly of the recoil restraint 50. A handle 56 is similarly attached to the tensioning strap along an attachment path V by stitches 57a. The handles 55 and 56 are each preferably provided by folding a length of PVC/polyester material around the outer end of each of the tensioning straps 14 and 15 and securing the PVC/polyester material with stitches to the respective outer ends of the tensioning straps. A preferred PVC/polyester material is 2207-68 from Ouimet Corporation. The handles 55 and 56 provide handholds for grasping by the user to adjust the tension of the tensioning straps 14 and 15. The handle 55 includes an engagement surface 58 formed of a hook material, such as VELCRO, for engaging the loop material of the front surface 26 of the end section 20 to releasably secure the handle 55 to the waist band and maintain the desired tension in the tensioning strap 14. The handle 56 likewise includes an engagement surface 59 for engaging the loop material of the front surface 30 of the end section 22. It will be appreciated that because each handle is located adjacent the outer end of its associated tensioning strap, the handles abut the recoil restraints 50 and 51, respectively, when the straps 14 and 15 are engaged by the restraints, such as when the handles are released from engagement from the band 12. In this manner, the travel of the recoiling handles is limited. This is advantageous for several reasons. Particularly, the handles are restrained from recoiling past the restraints and are thereby restrained from contacting the user or the waist band. This controlled limited movement of the handles which bear hook fastening material serves to prevent the hook material on the engagement surface of each handle from contacting the woven material of the mid portion of the waist band or the binding which may be damaged by forceful contact with the hook material. As mentioned previously, the restraints are each located a distance F from the anchoring member 43. The distance F is chosen to accommodate the preselected length of the straps 14 and 15 and is preferably greater than the fully relaxed length of the tensioning straps so that the straps are maintained in a slightly tensioned state (i.e. not slack) when they are "relaxed". Because of this slight tension, and the location of the recoil restraints, when the straps ends are released from the waist band and the handles contact the recoil restraints as the straps relax, the handles 55 and 56 project outwardly of the waist band 12 as shown in FIG. 6. In this position, it will be appreciated that the handles are easily located and are readily accessible for grasping by the user.

For purposes of ease of illustration, the waist band 12 depicted in several of the Figures is shown in its fully extended length position. It is to be recognized, however, that in a preferred embodiment, when the unattached ends of the tensioning straps 14 and 15 are released, the handles 55 and 56 contact their respective recoil restraints 50 and 51 prior to full relaxation of the straps so that when the belt is not in position about the waist of a user, the tensioning force of the straps 14 and 15 causes a slight wrinkling of the waist band 12 in the region between the loops (i.e. the midsection of the waist band). In this situation, the handles are in contact with the restraints but project from the plane of the waist band less than when the belt is about the waist of a wearer. In the latter instance, the handles project prominently from the plane of the waist band and in position for ready grasping by the wearer.

From the foregoing discussion of a preferred embodiment, it will be appreciated that the present invention provides an abdominal support belt wherein the pressure exerted on the abdomen by the belt is adjustable over a wide range so as to provide a belt which permits the selection by the user of the degree of support required. The user may obtain the desired support by simply adjusting the tension of the tensioning straps. The belt provides restraints for limiting the extent of return of the tension straps when they are detensioned. The belt also provides PVC/polyester material in areas of high wear to improve durability of the belt as well as protection against curling of the ends of the belt. The stays in the ends of the belt also aid in reducing curling of the ends.

As depicted in FIG. 1, the belt 10 is positioned around the abdomen of a user prior to engaging in activity. To install the belt, the user positions the belt 10 around the waist such that the waist band 12 is adjacent to the waist and the outer section of each tensioning strap 14 and 15 faces outwardly. The end section 20 of the waist band 12 is then positioned against the waist in the vicinity of the navel of the user such that the back surface 28 of the end section 20 is against and facing the waist and the front surface 26 of the end section 20 faces away from the waist. The end section 22 is then placed at least partially over the end section 20 such that hook material of the tip section 36 of the end section 22 engages the loop material of the front surface 26 of the end section 20 to secure the band 12 around the waist of the user. Optionally, a pair of braces 60 formed of a woven elastic material may be provided and positioned around the shoulders of the user to help maintain the relationship between the band 12 and the waist. As can be seen in FIG. 6, the handles 55 and 56 project outwardly from the waist band and are easily reached by the user when the waist band 12 is secured around the waist and the straps 14 and 15 are "relaxed".

Figure 7:
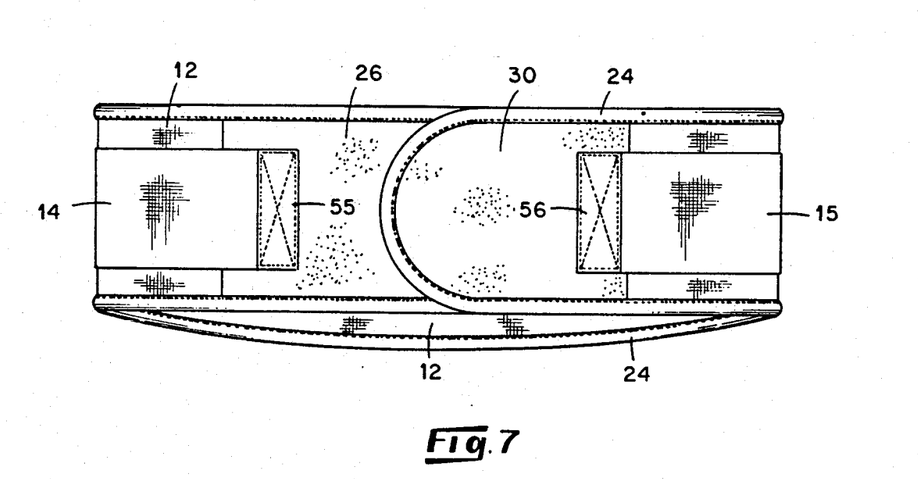
FIGS. 7 is a front elevational view of the belt of FIG. 1 showing the tensioninq strap in a tensioned state, with the handles secured to the waist band.

To select the desired degree of support, the user grasps the handles 55 and 56 and forces the handles towards one another in the direction of the abdominal midline of the user to tension the straps 14 and 15. When the desired amount of tension is effected, the engagement surface 58 of the handle 55 is preferably secured to the loop material of the front surface 26 of the end section 20 and the engagement surface 59 of the handle 56 is preferably secured to the loop material of the front surface 30 of the end section 22. In this regard, it will be understood that the objective is to secure the hook material provided on the engagement surfaces 58 and 59 to the loop material of one or more of the front surface(s) of the end sections to maintain the straps at the desired tension, as shown in FIG. 7. As mentioned above, FIG. 6 shows the waist band 12 positioned around the waist with the straps 14 and 15 in the "relaxed" state, it being understood that a slight tension exists in the straps because of the spacing provided between each recoil restraint and the anchoring member. As discussed, the handles project outwardly from the waist band 12 when the ends of the tensioning straps are released. In this position, the handles are readily accessible to the user for tensioning the straps. In addition, the recoil restraints also limit recoil of the tensioning straps when the handles are released from the waist band 12 to de-tension the straps. Thus it will be appreciated that the restraints prevent the handles from recoiling against the body of the user and also prevent the handles from striking the waist band 12 in a manner which would allow the hook material of the engagement surfaces to forcefully contact and thereby abrade the waist band 12 or the binding 24.

In addition to the advantages provided by the recoil restraints, it will be appreciated that the stays provided in the ends of the belt and the use of a PVC/polyester material in the aforementioned areas also provide advantages to the belt. Particularly, the stays serve to maintain the ends of the waist band flat and reduce inward curling of the ends. A reduction in curling is advantageous during assembly of the belt and also increases the life and appearance of the belt without compromising flexibility. The PVC/polyester material also improves the life and appearance of the belt without compromising flexibility. The PVC/polyester material offers improved resistance to scarring and has improved flexibility over conventional materials utilized in support belts. Particularly, the PVC/polyester material offers a construction material which is pliable and conformable to the waist of the user, yet also has sufficient body so as to resist curling and warpage after repeated use. In addition, placement of the material in accordance with the invention also provides cost and weight savings previously unattainable by known construction practices.

While this invention has been described in detail with particular reference to preferred embodiments thereof, it will be understood that variations and modifications can be made without departing from the spirit and scope of the invention as described hereinbefore and as defined in the following claims.

What is claimed is:

1. An improved abdominal support belt releasably securable around a user's waist, comprising:

an elongated waist band having first and second ends and first and second flat surfaces, said waist band being positionable around the user's waist with said first flat surface adjacent the user's waist and said second flat surface facing outwardly of the user's waist;

an elastic tensioning strap means anchored to said second flat surface of said waist band at an anchor point located generally midway between said first and second ends of said waist band, said elastic tensioning strap means comprising at least two flat members having oppositely disposed unanchored ends remote from said anchor point, said members including at least two generally parallel surfaces, said members being disposed in overlying relationship with one another with respective ones of their flat surfaces in facing relationship and with one of said members being disposed adjacent to and in overlying generally parallel relationship with said waist band, said flat members being joined to one another at said anchor point and at their opposite unanchored ends and being unattached to one another in the region between said anchor point and said opposite unanchored ends, said unanchored ends of said tensioning strap means being stretchable in a direction away from said anchor point and toward said first end of said waist band;

means joining the common overlying unanchored ends of said flat members to one another so that said flat members stretch and relax with one another;

means for releasably securing said unanchored ends of said elastic tensioning strap means to said waist band adjacent said first and second ends of said waist band when said unanchored ends of said tensioning strap means are stretched about the waist of the user; and at least two limiting means secured to said waist band, one each of said two limiting means being disposed on opposite sides of said anchor point for said tensioning strap means, each of said limiting means defining loop means including an unattached central portion, that one of said flat members of said tensioning strap means disposed next to said waist band being slidably received through a respective one of said loop means and the other of said flat members overlying said loop means, each of said limiting means being located on said waist band at a location between said anchor point and a respective one of the opposite ends of said waist band, said location being a distance from said anchor point that is substantially equal to a relaxed length of that flat member of said tensioning strap means that is received through said loop means such that when that unanchored end of said tensioning strap means received through said loop means is not materially stretched, the secured end of said tensioning strap means engages said central portion of said loop means thereby securing said end of said tensioning strap means in a position adjacent to said waist band and recoil of said unanchored end of said tensioning strap means toward said anchor point when said end is released from securement adjacent said waist band is limited.

2. The belt of claim 1 wherein said loop means comprises at least one loop secured to said waist band adjacent the first end of said waist band.

3. The belt of claim 1 wherein said strap includes a semi-rigid member adjacent said unattached end and said semi-rigid member contacts said limiting means during recoil of said strap.

4. The belt of claim 3 wherein when said semi-rigid member contacts said limiting means, said semi-rigid member is caused to project away from said waist band and in position for grasping by the user.

5. The belt of claim 1, further comprising stay means operatively associated with at least one of said ends of said waist band for inhibiting curling of at least one of said ends.

6. The belt of claim 5, wherein said first end has front surface and a back surface and said stay means comprises a resilient, elongate bendable stay having its length axis positioned horizonatally between said front and back surface.

7. The belt of claim 6, wherein at least a portion of said back or front surfaces is formed of an expanded cast polyvinyl chloride/polyester material.

8. The belt of claim 1, wherein the distance of each of said limiting means from said anchor point is slightly greater than the relaxed length of that portion of said tensioning strap means which is disposed on a respective side of said anchor point so that when an unanchored end of said tensioning strap means is released from securement to an end of said waist band, recoil of said portion of said tensioning strap means is limited to less than full return of said portion of said tensioning strap means to its relaxed state.

9. The belt of claim 1, whereby when said portion of said tension strap means is unanchored, said handle means is caused to be oriented so that the handle is positioned for ready grasping by the user.

10. The belt of claim 1, wherein said means joining the common overlying ends of the overlying flat members of said tensioning strap means defines a generally flat handle means.

11. The belt of claim 10, whereby when said portion of said tension strap means is unanchored, said handle means is caused to be oriented so that the handle is positioned for ready grasping by the user.

* * * * *